(12) United States Patent
Hunt

(10) Patent No.: US 8,580,250 B2
(45) Date of Patent: *Nov. 12, 2013

(54) BOTULINUM TOXIN COMPOSITIONS

(75) Inventor: Terrence J. Hunt, Temecula, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/566,804

(22) Filed: Aug. 3, 2012

(65) Prior Publication Data

US 2012/0301455 A1 Nov. 29, 2012

Related U.S. Application Data

(63) Continuation of application No. 11/195,268, filed on Aug. 1, 2005.

(51) Int. Cl.
*A61K 9/19* (2006.01)

(52) U.S. Cl.
USPC ........................................ 424/94.3; 424/94.67

(58) Field of Classification Search
None
See application file for complete search history.

(56) References Cited

U.S. PATENT DOCUMENTS

| | | | |
|---|---|---|---|
| 5,512,547 A | 4/1996 | Johnson et al. | 514/21 |
| 5,696,077 A | 12/1997 | Johnson et al. | 514/2 |
| 5,756,468 A | 5/1998 | Johnson et al. | 514/21 |
| 6,034,221 A | 3/2000 | Berezenko et al. | 530/362 |
| 6,087,327 A | 7/2000 | Pearce et al. | 514/2 |
| 7,579,010 B2 * | 8/2009 | Hunt | 424/236.1 |
| 8,323,666 B2 * | 12/2012 | Hunt | 424/239.1 |
| 2003/0118598 A1 * | 6/2003 | Hunt | 424/184.1 |
| 2004/0086531 A1 | 5/2004 | Barron | 424/239.1 |
| 2004/0086532 A1 | 5/2004 | Donovan | 424/239.1 |
| 2007/0026019 A1 | 2/2007 | Hunt | 424/239.1 |
| 2007/0134199 A1 * | 6/2007 | Frevert | 424/85.4 |

FOREIGN PATENT DOCUMENTS

| | | | |
|---|---|---|---|
| CN | 1215084 A | 4/1999 | C12P 21/00 |
| EP | 361 991 | 8/1989 | C12P 21/02 |
| EP | 330 451 | 2/1998 | C12N 15/00 |
| EP | 1 112 082 | 4/2001 | A61K 38/16 |
| WO | WO 00/15245 | 3/2000 | |
| WO | WO 2004/060384 | 7/2004 | |
| WO | WO 2006/116302 | 11/2006 | |
| WO | 2008/070538 | * 6/2008 | A61K 9/107 |

OTHER PUBLICATIONS

Boor, Alden, et al., *Effects of Salts and Colloids on Potency of Botulinum Toxin*, Proc Soc Exp Biol Med., Jun. 1955;89(2), pp. 270-272.
Borodic, Gary, et al., *Botulinum toxin therapy, immunologic resistance, and problems with available materials*, Neurology, Jan. 46(1), 1996, pp. 26-29.
BOTOX® Product Information Sheet, 2000.
BOTOX® Product Information Sheet, http://www.botoxcosmetic.com/resources/pi.aspx, Approved, Apr. 12, 2000.
BOTOX® package insert, Jun. 2004.

(Continued)

*Primary Examiner* — Albert Navarro
*Assistant Examiner* — Ginny Portner
(74) *Attorney, Agent, or Firm* — Brigitte C. Phan; Kenton B. Abel; Allergan, Inc.

(57) ABSTRACT

A high potency botulinum toxin pharmaceutical composition comprising two excipients (such as albumin and sodium chloride) in a weight to weight ratio of between about 1 and about 100.

6 Claims, 2 Drawing Sheets

(56) References Cited

OTHER PUBLICATIONS

Carpenter et al., *Interactions of Stabilizing Additives with Proteins During Freeze-Thawing and Freeze-Drying*, International Symposium on Biological Product Freeze-Drying and Formulation, Oct. 24-26, 1990; Karger (1992), 225-239.

DYSPORT® product sheet, Oct. 11, 2003.

Goodnough M.C., et al., *Recovery of type-A botulinal toxin following lyophilization*, Acs Symposium Series 1994;567(-):193-203.

Goodnough M.C., et al., *Stabilization of botulinum toxin type A during lyophilization*, Appl Environ Microbiol 1992;58(10):3426-3428.

Kobayashi K., et al., *The development of recombinant human serum albumin*, Ther Apher Nov. 1998;2(4):257-62.

Kohl A., et al., *Comparison of the effect of botulinum toxin A (Botox (R)) with the highly-purified neurotoxin (NT 201) in the extensor digitorum brevis muscle test*, Mov Disord 2000; 15(Suppl 3):165.

MYCOBLOC® Product Information Sheet, Solstice NeuroSciences, Rev. Nov. 2004.

Naumann, Markus, et al., *European J. Neurology* 6 (Supp 4): S111-S115:1999.

Ohtani W., et al., *Physicochemical and immunochemical properties of recombinant human serum albumin from Pichia pastoris*, Anal Biochem Feb. 1, 1998;256(1):56-62.

Peters, T., Jr., *All About Albumin Biochemistry, Genetics and Medical Applications*, Academic Press (1996), pp. 295 and 298.

Rader R.A., *Botulinum toxin A*, in Ronald Rader, ed. *BIOPHARMA: Biopharmaceutical Products in the U.S. Market* Rockville, MD: Biotechnology Information Institute; 2001:pp. 271-274 (332).

Rader R.A., *Botulinum toxin B*, in Ronald Rader, ed. *BIOPHARMA: Biopharmaceutical Products in the U.S. Market* Rockville, MD: Biotechnology Information Institute; 2001:pp. 274-276 (333).

Ragona et al., *The Laryngoscope* 109:1344-1346:1999.

Schantz, E.J., et al, *Properties and use of Botulinum toxin and Other Microbial Neurotoxins in Medicine*, Microbiol Rev. 56: 80-99 (1992).

Schmidt, et al., *Endoproteinase Activity of Type A Botulinum Neurotoxin Substrate Requirements and Activation by Serum Albumin*, J. of Protein Chemistry, 16 (1), 19-26 (1997).

Singh, *Critical Aspects of Bacterial Protein Toxins*, pp. 63-84 (chapter 4) of Natural Toxins II, edited by B.R. Singh et al., Plenum Press, New York (1976).

Wohlfarth, Kai et al., *Pharmacokinetic properties of different formulations of botulinum neurotoxin type A*, Movement Disord., Mar. 2004, vol. 19, Suppl. 8, pp. S65-S67.

\* cited by examiner

Figure 1

Botulinum Neurotoxin Complex

Type A 900 kD Complex

- Composition of complex
  - Neurotoxic protein (about 150 kD)
  - May contain nontoxic hemagglutinin (NTHA) and nontoxic nonhemagglutinin proteins (NTNH)
- Complex sizes
  - 900 kD: only type A
  - 500 kD: types A, B, $C_1$, D
  - 300 kD: types A, B, $C_1$, D, E, F

Figure 2

Potency as a Function of NaCl
(500ug HSA Constant)

% Recovery vs Normalized NaCl (900ug=1)

BOTULINUM TOXIN COMPOSITIONS

CROSS REFERENCE

This application is a continuation of application Ser. No. 11/195,268 filed Aug. 1, 2005, the entire contents of which application is incorporated herein by reference.

BACKGROUND

The present invention relates to improved botulinum toxin pharmaceutical compositions. In particular, the present invention relates to botulinum toxin pharmaceutical compositions with an increased potency.

A pharmaceutical composition is a formulation which contains at least one active ingredient (such as for example a Clostridial toxin, such as a botulinum neurotoxin) as well as, for example, one or more excipients, buffers, carriers, stabilizers, preservatives and/or bulking agents, and is suitable for administration to a patient to achieve a desired effect or result. The pharmaceutical compositions disclosed herein can have diagnostic, therapeutic, cosmetic and/or research utility in various species, such as for example in human patients or subjects.

For storage stability and convenience of handling, a pharmaceutical composition can be formulated as a lyophilized (i.e. freeze dried) or vacuum dried powder which can be reconstituted with a suitable fluid, such as saline or water, prior to administration to a patient. Alternately, the pharmaceutical composition can be formulated as an aqueous solution or suspension. A pharmaceutical composition can contain a proteinaceous active ingredient. Unfortunately, a protein active ingredient can be very difficult to stabilize (i.e. maintained in a state where loss of biological activity is minimized), resulting therefore in a loss of protein and/or loss of protein activity during the formulation, reconstitution (if required) and during the period of storage prior to use of a protein containing pharmaceutical composition. Protein active ingredient stability problems can occur because of denaturation, degradation, dimerization, and/or polymerization of the protein. Various excipients, such as albumins, gelatins, polysaccharides and amino acids (native or recombinant) have been used with differing degrees of success to try and stabilize a protein active ingredient present in a pharmaceutical composition. Additionally, cryoprotectants such as alcohols have been used to reduce protein denaturation under the freezing conditions of lyophilization.

Albumins are small, abundant plasma proteins. Human serum albumin has a molecular weight of about 69 kiloDaltons (kD) and has been used as a non-active ingredient in a pharmaceutical composition where it can serve as a bulk carrier and stabilizer of certain protein active ingredients present in a pharmaceutical composition.

The stabilization function of albumin in a pharmaceutical composition can be present both during the multi-step formulation of the pharmaceutical composition and upon the later reconstitution of the formulated pharmaceutical composition. Thus, stability can be imparted by albumin to a proteinaceous active ingredient in a pharmaceutical composition by, for example, (1) reducing adhesion (commonly referred to as "stickiness") of the protein active ingredient to surfaces, such as the surfaces of laboratory glassware, vessels, to the vial in which the pharmaceutical composition is reconstituted and to the inside surface of a syringe used to inject the pharmaceutical composition. Adhesion of a protein active ingredient to surfaces can lead to loss of active ingredient and to denaturation of the remaining retained protein active ingredient, both of which reduce the total activity of the active ingredient present in the pharmaceutical composition, and; (2) reducing denaturation of the active ingredient which can occur upon preparation of a low dilution solution of the active ingredient.

As well as being able to stabilize a protein active ingredient in a pharmaceutical composition, human serum albumin also has the advantage of generally negligible immunogenicity when injected into a human patient. A compound with an appreciable immunogenicity can cause the production of antibodies against it which can lead to an anaphylactic reaction and/or to the development of drug resistance, with the disease or disorder to be treated thereby becoming potentially refractory to the pharmaceutical composition which has an immunogenic component. Gelatin has been used in some protein active ingredient pharmaceutical compositions as an albumin substitute.

Botulinum Toxin

The anaerobic, gram positive bacterium *Clostridium botulinum* produces a potent polypeptide neurotoxin, botulinum toxin, which causes a neuroparalytic illness in humans and animals referred to as botulism. *Clostridium botulinum* and its spores are commonly found in soil and the bacterium can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of botulinum toxin (purified neurotoxin complex) type A is a $LD_{50}$ in mice. Interestingly, on a molar basis, botulinum toxin type A is 1.8 billion times more lethal than diphtheria, 600 million times more lethal than sodium cyanide, 30 million times more lethal than cobrotoxin and 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18-20 grams each. In other words, one unit of botulinum toxin is the amount of botulinum toxin that kills 50% of a group of female Swiss Webster mice. Seven generally immunologically distinct botulinum neurotoxins have been characterized, these being respectively botulinum neurotoxin serotypes A, B, $C_1$, D, E, F, and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. The botulinum toxins apparently bind with high affinity to cholinergic motor neurons, are translocated into the neuron and block the presynaptic release of acetylcholine.

Botulinum toxins have been used in clinical settings for the treatment of neuromuscular disorders characterized by hyperactive skeletal muscles. Botulinum toxin type A was approved by the U.S. Food and Drug Administration in 1989 for the treatment of essential blepharospasm, strabismus and hemifacial spasm in patients over the age of twelve. Clinical effects of peripheral injection (i.e. intramuscular or subcutaneous) botulinum toxin type A are usually seen within one week of injection, and often within a few hours after injection. The typical duration of symptomatic relief (i.e. flaccid muscle paralysis) from a single intramuscular injection of botulinum toxin type A can be about three months to about six months.

Although all the botulinum toxins serotypes apparently inhibit release of the neurotransmitter acetylcholine at the neuromuscular junction, they do so by affecting different neurosecretory proteins and/or cleaving these proteins at different sites. Botulinum toxin A is a zinc endopeptidase which can specifically hydrolyze a peptide linkage of the intracellular, vesicle associated protein SNAP-25. Botulinum type E also cleaves the 25 kiloDalton (kD) synaptosomal associated protein (SNAP-25), but targets different amino acid sequences within this protein, as compared to botulinum toxin type A. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (H chain) and a cell surface receptor; the receptor is thought to be different for each serotype of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of botulinum toxin activity appears to involve reduction of the disulfide bond joining the H and L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ are apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemagglutinin protein and a non-toxin and non-toxic nonhemagglutinin protein. These two non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The toxin complexes can be dissociated into toxin protein and hemagglutinin proteins by treating the complex with red blood cells at pH 7.3. The toxin protein has a marked instability upon removal of the hemagglutinin protein.

All the botulinum toxin serotypes are made by *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

High quality crystalline botulinum toxin type A can be produced from the Hall A strain of *Clostridium botulinum* with characteristics of $\geq 3\times 10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E.

J., et al, *Properties and use of Botulinum toxin and Other Microbial Neurotoxins in Medicine*, Microbiol Rev. 56: 80-99 (1992). Generally, the botulinum toxin type A complex can be isolated and purified from an anaerobic fermentation by cultivating *Clostridium botulinum* type A in a suitable medium. Raw toxin can be harvested by precipitation with sulfuric acid and concentrated by ultramicrofiltration. Purification can be carried out by dissolving the acid precipitate in calcium chloride. The toxin can then be precipitated with cold ethanol. The precipitate can be dissolved in sodium phosphate buffer and centrifuged. Upon drying there can then be obtained approximately 900 kD crystalline botulinum toxin type A complex with a specific potency of $3 \times 10^7$ $LD_{50}$ U/mg or greater. This known process can also be used, upon separation out of the non-toxin proteins, to obtain pure botulinum toxins, such as for example: purified botulinum toxin type A with an approximately 150 kD molecular weight with a specific potency of $1-2 \times 10^8$ $LD_{50}$ U/mg or greater; purified botulinum toxin type B with an approximately 156 kD molecular weight with a specific potency of $1-2 \times 10^8$ $LD_{50}$ U/mg or greater, and; purified botulinum toxin type F with an approximately 155 kD molecular weight with a specific potency of $1-2 \times 10^7$ $LD_{50}$ U/mg or greater.

A pure (i.e. 150 kDa botulinum toxin free of the non-toxin complex proteins) can be obtained by loading a solution of a botulinum toxin complex onto a suitable ion exchange chromatograph in a pH 8 buffer to disassociate the non toxin complex proteins from the 150 kDa botulinum toxin molecule, thereby providing (in the flow through from the column) a solution of a botulinum toxin neurotoxic component with an approximately 150 kD molecular weight.

Pure botulinum toxin (i.e. the approximately 150 kDa molecular weight neurotoxic component of a botulinum toxin complex) has been used to treat humans. See e.g. Kohl A., et al., *Comparison of the effect of botulinum toxin A (Botox (R)) with the highly-purified neurotoxin (NT 201) in the extensor digitorum brevis muscle test*, Mov Disord 2000; 15(Suppl 3):165. Hence, a botulinum toxin pharmaceutical composition can be prepared using a pure (approx 150 kDa) botulinum toxin, as opposed to use of a botulinum toxin complex. A pure botulinum toxin type A is available from Merz Pharmaceuticals under the tradename XEOMIN.

Already prepared and purified botulinum toxins and toxin complexes suitable for preparing pharmaceutical formulations can be obtained from List Biological Laboratories, Inc., Campbell, Calif.; the Centre for Applied Microbiology and Research, Porton Down, U.K.; Wako (Osaka, Japan), as well as from Sigma Chemicals of St Louis, Mo.

Examples of clinical use of a botulinum toxin are:
(1) about 75-125 units of BOTOX®[1] per intramuscular injection (multiple muscles) to treat cervical dystonia;

[1]Available from Allergan, Inc., of Irvine, Calif. under the tradename BOTOX®.

(2) 5-10 units of BOTOX® per intramuscular injection to treat glabellar lines (brow furrows) (5 units injected intramuscularly into the procerus muscle and 10 units injected intramuscularly into each corrugator supercilii muscle);
(3) about 30-80 units of BOTOX® to treat constipation by intrasphincter injection of the puborectalis muscle;
(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).
(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.
(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111-S1150: 1999), and in some circumstances for as long as 27 months. *The Laryngoscope* 109:1344-1346: 1999. However, the usual duration of the effect of an intramuscular injection of Botox® is typically about 3 to 4 months.

The success of botulinum toxin type A to treat a variety of clinical conditions has led to interest in other botulinum toxin serotypes. European patent EPI 112082 ("Stable liquid formulations of botulinum toxin"), issued Jul. 31, 2002 claims a stable liquid pharmaceutical botulinum toxin formulation comprising a buffer (pH 5-6) and a botulinum toxin, wherein the toxin formulation is stable as a liquid for at least one year at temperatures between 0-10 C or at least 6 months at temperatures between 10 and 30 C. Such a botulinum toxin pharmaceutical formulation (an embodiment of which is sold commercially under the tradename MyoBloc® or NeuroBloc® by Solstice Neurosciences, Inc., of San Diego, Calif.) is prepared as a liquid solution (no lyophilization or vacuum drying is carried out) which does not require reconstitution before use.

Chinese patent application CN 1215084A discusses an albumin free botulinum toxin type A formulated with gelatin, an animal derived protein. U.S. Pat. No. 6,087,327 also discloses a composition of botulinum toxin types A and B formulated with gelatin.

U.S. Pat. No. 5,512,547 (Johnson et al) entitled "Pharmaceutical Composition of Botulinum Neurotoxin and Method of Preparation" issued Apr. 30, 1996 and claims a pure botulinum type A formulation comprising albumin and trehalose, storage stable at 37 degrees C.

U.S. Pat. No. 5,756,468 (Johnson et al) issued May 26, 1998 ("Pharmaceutical Compositions of Botulinum Toxin or Botulinum Neurotoxin and Method of Preparation"), and claims a lyophilized botulinum toxin formulation comprising a thioalkyl, albumin and trehalose which can be stored between 25 degrees C. and 42 degrees C.

U.S. Pat. No. 5,696,077 (Johnson et al) entitled "Pharmaceutical Composition Containing Botulinum B Complex" issued Dec. 9, 1997 and claims a freeze dried, sodium chloride-free botulinum type B complex formation comprising a type B complex and a protein excipient.

U.S. patent application publication number 2003 0118598 (Hunt) discloses uses of various excipients such as a recombinant albumin, collagen or a starch to stabilize a botulinum toxin.

Goodnough M. C., et al., *Stabilization of botulinum toxin type A during lyophilization*, Appl Environ Microbiol 1992; 58(10):3426-3428, and; Goodnough M. C., et al., *Recovery of type-A botulinal toxin following lyophilization*, Acs Symposium Series 1994; 567(–):193-203, disclose botulinum toxin formulations comprising albumin and sodium chloride in a ratio of about 0.6:1 (i.e. 5 mg of BSA or HSA per ml and 9 mg of NaCl per ml of reconstituted botulinum toxin solution) and state that elimination of sodium chloride from the botulinum toxin formulation (and increasing the HSA to as much as 9 mg/ml in the salt free formulations) contributed significantly to obtaining a formulation with active botulinum toxin.

The botulinum toxin molecule (about 150 kDa), as well as the botulinum toxin complexes (about 300-900 kDa), such as the toxin type A complex are extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) are dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the botulinum toxin may be used months or years after the botulinum toxin containing pharmaceutical composition is formulated, the botulinum toxin must be stabilized with a stabilizing agent, such as an albumin or gelatin. Additionally, for storage stability botulinum toxin can be processed into a solid state (i.e. a powder) by known lyophilization or vacuum-drying techniques.

Furthermore, any one of the harsh pH, temperature and concentration range conditions required to lyophilize (freeze-dry) or vacuum dry a botulinum toxin containing pharmaceutical composition into a toxin shipping and storage format (ready for use or reconstitution by a physician) can detoxify the toxin. Thus, gelatin and serum albumin have been used with some success to stabilize botulinum toxin.

A commercially available botulinum toxin containing pharmaceutical composition is sold under the trademark BOTOX® (available from Allergan, Inc., of Irvine, Calif.). BOTOX® consists of a purified botulinum toxin type A complex, human serum albumin, and sodium chloride packaged in sterile, vacuum-dried form. The botulinum toxin type A is made from a culture of the Hall strain of *Clostridium botulinum* grown in a medium containing N—Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A complex, 0.5 milligrams of human serum albumin and 0.9 milligrams of sodium chloride in a sterile, vacuum-dried form without a preservative.

To reconstitute vacuum-dried BOTOX® sterile normal saline without a preservative (0.9% Sodium Chloride injection) is used by drawing up the proper amount of diluent in the appropriate size syringe. Since BOTOX® is denatured by bubbling or similar violent agitation, the diluent is gently injected into the vial. For sterility reasons, BOTOX® should be administered within about 72 hours after reconstitution. During this time period, reconstituted BOTOX® is stored in a refrigerator (2° to 8° C.). Reconstituted BOTOX® is clear, colorless and free of particulate matter. The vacuum-dried product is stored in a freezer or refrigerator.

Other commercially available botulinum toxin containing pharmaceutical compositions include Dysport® (*Clostridium botulinum* type A toxin hemagglutinin complex with human serum albumin and lactose in the formulation, available from Ipsen Limited, Berkshire, U.K. as a powder to be reconstituted with 0.9% sodium chloride before use), and MyoBloc™ (an injectable solution comprising botulinum toxin type B, human serum albumin, sodium succinate, and sodium chloride at about pH 5.6, available from Elan Corporation, Dublin, Ireland).

It has been reported that a suitable alternative to human serum albumin as a botulinum toxin stabilizer may be another protein or alternatively a low molecular weight (non-protein) compound. Carpender et al., *Interactions of Stabilizing Additives with Proteins During Freeze-Thawing and Freeze-Drying*, International Symposium on Biological Product Freeze-Drying and Formulation, 24-26 Oct. 1990; Karger (1992), 225-239.

Human serum albumin is believed to function in a pharmaceutical composition as more than a mere bulking agent. Thus, albumin apparently can interact with botulinum toxin so as to increase the potency of the neurotoxin. For example, it is known that bovine serum albumin can act as more than a mere stabilizing excipient for botulinum toxin type A, since bovine serum albumin apparently also accelerates the rate of catalysis of synthetic peptide substrates, which substrates resemble the SNAP-25 intraneuronal substrate for botulinum toxin type A Schmidt, et al., *Endoproteinase Activity of Type A Botulinum Neurotoxin Substrate Requirements and Activation by Serum Albumin*, J. of Protein Chemistry, 16 (1), 19-26 (1997). Thus, albumin may have a potentiating effect, apparently by affecting rate kinetics, upon the intracellular proteolytic action of a botulinum toxin upon the toxin's substrate. This potentiating effect may be due to albumin which has accompanied the botulinum toxin upon endocytosis of the toxin into a target neuron or the potentiating effect may be due to the pre-existing presence cytoplasmic albumin within the neuron protein prior to endocytosis of the botulinum toxin.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

Thus, what is needed is a process for preparing a botulinum toxin pharmaceutical formulation where little or no botulinum toxin is lost during the compounding process. Alternately stated, what is needed is a process for preparing a botulinum toxin pharmaceutical formulation which permits a high recovery of the botulinum toxin after reconstitution.

Loss of botulinum toxin during compounding (which leads to a lower recovery) presents the possibility of inactivated toxin (toxoid) being present in the final reconstituted product, thereby raising an antigenic potential of the product upon administration to a patient. The theoretical optimal is to have 100% of the botulinum toxin which enters the compounding process present in the final reconstituted product and present as biologically active botulinum toxin.

What is also needed therefore is a botulinum toxin containing pharmaceutical composition with a higher potency, as compared to the potencies of known botulinum toxin pharmaceutical compositions. Expressed in an alternate manner, what is needed is a botulinum toxin pharmaceutical composition with a higher potency of the botulinum toxin for each nanogram of the botulinum toxin present in the botulinum toxin pharmaceutical composition.

SUMMARY

The present invention meets this need by providing a process for preparing a botulinum toxin pharmaceutical formulation wherein little or no botulinum toxin is lost during the compounding process. Alternately stated, a process within the scope of the present invention permits preparation of a botulinum toxin pharmaceutical formulation with a high recovery of the botulinum toxin after reconstitution. Significantly, processes within the scope of the present invention approach the theoretical optimum by permitting about 100% of the botulinum toxin which enters the compounding process to be present in the final reconstituted product as biologically active botulinum toxin.

Additionally the present invention meets the needs expressed above by providing a botulinum toxin pharmaceutical composition with a higher (that is an increased) potency, as compared to the potencies of known botulinum toxin pharmaceutical compositions. In particular, the present invention meets this need by providing a powdered (due for example to freeze drying, lyophilization and/or vacuum drying) botulinum toxin pharmaceutical composition which upon (i.e. after) reconstitution with an aqueous fluid (such as saline or water) has an increased potency (as determined for example by the mouse $LD_{50}$ assay), as compared to the potency after reconstitution with an aqueous fluid of a known powdered botulinum toxin pharmaceutical composition (such as Botox® or Dysport®). Potency upon reconstitution can be referred to as potency after "recovery". Hence, the present invention includes a botulinum toxin pharmaceutical composition with an increased potency upon recovery, or synonymously with an increased recovered or recovery potency.

Briefly, an important aspect of the present invention for meeting these dual needs of a high conservation (i.e. low or small loss) of the amount of the botulinum toxin which enters a compounding process (as compared to the amount of active botulinum toxin present in the final [compounded] product), and a high botulinum toxin pharmaceutical composition recovered potency, is achieved by compounding the solid form botulinum toxin pharmaceutical composition such that two of the excipients present in the botulinum toxin pharmaceutical composition are present, at least during the compounding process, in a particular weight to weight ratio or in a particular weight to weight ratio range.

DEFINITIONS

As used herein, the words or terms set forth below have the following definitions.

"About" means that the item, parameter or term so qualified encompasses a range of plus or minus ten percent above and below the value of the stated item, parameter or term.

"Administration", or "to administer" means the step of giving (i.e. administering) a pharmaceutical composition to a subject. The pharmaceutical compositions disclosed herein are "locally administered". Systemic (i.e. intravenous or oral) routes of administration are excluded from the scope of the present invention, to the extent that a systemic administration would result in systemic effects of a systemically administered active ingredient. Systemic administration of a targeted active ingredient which does not result in systemic effects is not excluded from the scope of the present invention (see e.g. published U.S. patent applications 20040086532 and 20040086531). Local administration includes, but is not limited to, intramuscular (i.m.) administration, intradermal or subdermal administration, subcutaneous administration, intrathecal administration, intraperitoneal (i.p.) administration, topical contact, and implantation of a slow-release device such as polymeric implant or miniosmotic pump.

"Botulinum toxin" means a neurotoxin produced by Clostridium botulinum, as well as a botulinum toxin (or the light chain or the heavy chain thereof) made recombinantly by a non-Clostridial species. The phrase "botulinum toxin", as used herein, encompasses the botulinum toxin serotypes A, B, C, D, E, F and G. Botulinum toxin, as used herein, also encompasses both a botulinum toxin complex (i.e. the 300, 600 and 900 kDa complexes) as well as the purified botulinum toxin (i.e. about 150 kDa). "Purified (or pure) botulinum toxin" is defined as a botulinum toxin that is isolated, or substantially isolated, from other proteins, including proteins that form a botulinum toxin complex. A purified (or pure) botulinum toxin can be greater than 95% pure, and preferably is greater than 99% pure.

"Clostridial neurotoxin" means a neurotoxin produced from, or native to, a Clostridial bacterium, such as Clostridium botulinum, Clostridium butyricum or Clostridium beratti, as well as a Clostridial neurotoxin made recombinantly by a non-Clostridial species.

"Enhanced potency" with regard to a botulinum toxin containing pharmaceutical composition means that the composition has a potency (as determined, for example, by the mouse $LD_{50}$ assay) which is from at least 5% and up to 50%, or more, greater than the potency of a reference botulinum toxin pharmaceutical composition. A reference botulinum toxin pharmaceutical composition can contain a botulinum toxin, sodium chloride and HSA, wherein the albumin and the sodium chloride are present in a weight to weight ratio of about 0.6:1.

"Entirely free (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Excipient" means a substance present in a pharmaceutical composition other than the active pharmaceutical ingredient present in the pharmaceutical composition. An excipient can be a buffer, carrier, stabilizer, preservative, diluent, vehicle, and/or a bulking agent, such as an albumin, gelatin, collagen and/or sodium chloride.

"Immobilizing" means a step that prevents a subject from moving one or more body parts. If a sufficient number of body parts are immobilized, the subject will accordingly be immobilized. Thus, "immobilizing" encompasses the immobilization of a body part, such as a limb, and/or the complete immobilization of a subject.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Patient" means a human or non-human subject receiving medical or veterinary care. Accordingly, as disclosed herein, the compositions may be used in treating any animal, such as mammals.

"Pharmaceutical composition" means a formulation in which an active ingredient can be a neurotoxin, such as a Clostridial neurotoxin. The word "formulation" means that there is at least one additional ingredient in the pharmaceutical composition besides a neurotoxin active ingredient. A pharmaceutical composition is therefore a formulation which is suitable for diagnostic, therapeutic or cosmetic use (i.e. by intramuscular or subcutaneous injection or by insertion of a depot or implant) to a subject, such as a human patient. The pharmaceutical composition can be: in a lyophilized or vacuum dried condition; a solution formed after reconstitution of the lyophilized or vacuum dried pharmaceutical composition with saline or water, or; as a solution which does not require reconstitution. The neurotoxin active ingredient can be one of the botulinum toxin serotypes A, B, $C_1$, D, E, F or G or a tetanus toxin, all of which can be made natively by Clostridial bacteria. As stated, a pharmaceutical composition can be liquid or solid, for example vacuum-dried. The constituent ingredients of a pharmaceutical composition can be included in a single composition (that is all the constituent ingredients, except for any required reconstitution fluid, are present at the time of initial compounding of the pharmaceutical composition) or as a two-component system, for example a vacuum-dried composition reconstituted with a diluent such as saline which diluent contains an ingredient (such as water) not present in the initial compounding of the pharmaceutical composition.

"Polysaccharide" means a polymer of more than two saccharide molecule monomers, which monomers can be identical or different.

"Protein stabilizer" (or "primary stabilizer") is a chemical agent that assists to preserve or maintain the biological structure (i.e. the three dimensional conformation) and/or biological activity of a protein (such as a Clostridial neurotoxin, such as a botulinum toxin). Stabilizers can be proteins or polysaccharides. Examples of protein stabilizers include hydroxyethyl starch (hetastarch), serum albumin, gelatin, collagen, as well as a recombinant albumin, gelatin or collagen. As disclosed herein, the primary stabilizer can be a synthetic agent that would not produce an immunogenic response (or produces an attenuated immune response) in a subject receiving a composition containing the primary stabilizer. In other embodiments of the invention, the protein stabilizers may be proteins from the same species of animal that is being administered the protein. Additional stabilizers may also be included in a pharmaceutical composition. These additional or secondary stabilizers may be used alone or in combination with primary stabilizers, such as proteins and polysaccharides. Exemplary secondary stabilizers include, but are not limited to non-oxidizing amino acid derivatives (such as a tryptophan derivate, such as N-acetyl-tryptophan ("NAT")), caprylate (i.e. sodium caprylate), a polysorbate (i.e. P80), amino acids, and divalent metal cations such as zinc. A pharmaceutical composition can also include preservative agents such as benzyl alcohol, benzoic acid, phenol, parabens and sorbic acid. A "recombinant stabilizer" is a "primary stabilizer" made by recombinant means, such as for example, a recombinantly made albumin (such as a recombinantly made human serum albumin), collagen, gelatin or a cresol, such as an M-cresol.

"Stabilizing", "stabilizes", or "stabilization" mean that a pharmaceutical active ingredient ("PAI") retains at least 20% and up to 100% of its biological activity (which can be assessed as potency or as toxicity by an in vivo $LD_{50}$ or $ED_{50}$ measure) in the presence of a compound which is stabilizing, stabilizes or which provides stabilization to the PAI. For example, upon (1) preparation of serial dilutions from a bulk or stock solution, or (2) upon reconstitution with saline or water of a lyophilized, or vacuum dried botulinum toxin containing pharmaceutical composition which has been stored at or below about −2 degrees C. for between six months and four years, or (3) for an aqueous solution botulinum toxin containing pharmaceutical composition which has been stored at between about 2 degrees and about 8 degrees C. for from six months to four years, the botulinum toxin present in the reconstituted or aqueous solution pharmaceutical composition has (in the presence of a compound which is stabilizing, stabilizes or which provides stabilization to the PAI) greater than about 20% and up to about 100% of the potency or toxicity that the biologically active botulinum toxin had prior to being incorporated into the pharmaceutical composition.

"Substantially free" means present at a level of less than one percent by weight of the pharmaceutical composition.

"Therapeutic formulation" means a formulation can be used to treat and thereby alleviate a disorder or a disease, such as a disorder or a disease characterized by hyperactivity (i.e. spasticity) of a peripheral muscle.

A pharmaceutical composition within the scope of my invention can comprise a Clostridial toxin, such as a botulinum toxin, and an excipient which acts to stabilize the toxin A pharmaceutical composition within the scope of my invention can also consist essentially of a botulinum toxin, and a stabilizer. Additionally, pharmaceutical composition within the scope of my invention can consist of a botulinum toxin, and a recombinant stabilizer.

The botulinum toxin can be present as a botulinum toxin complex (i.e. as an approximately 300 kiloDalton to about 900 kiloDalton complex, depending upon the particular botulinum toxin serotype used) or the botulinum toxin can be is present as a pure or purified botulinum toxin (meaning present as the about 150 kiloDalton neurotoxic component of a botulinum toxin complex) which is free, substantially or essentially free of any botulinum toxin complex protein (i.e. removed from association the HA and NTNH proteins). Thus, as shown by FIG. 1, a botulinum toxin made naturally by the *Clostridium botulinum* bacterium is typically made as a complex comprising the botulinum toxin molecule (a protein with a molecular weight of about 150 kiloDaltons) (also referred to as the neurotoxic component) and an array of non-toxic proteins (haemaglutinins and non-haemaglutinins) in a close, though non-covalent association with the neurotoxic component. Thus, as shown by FIG. 1, there can be up to about seven non-neurotoxic molecules (total weight about 750 kDa) associated (non-covalently) with the (about 150 kDa) neurotoxic component to form a 900 kDa botulinum neurotoxin type A complex. In FIG. 1: HA=NTHA=a non-toxic haemaglutinin; LC=light chain (about 50 kDa); HC=heavy chain (about 100 kDa); —S—S—=the single disulphide bond which joins the LC and the HC, and; Zn=a zinc atom (botulinum toxin is a zinc endopeptidase). Hence, LC plus HC is a molecule with a molecular weight of about 150 kDa, and this is the neurotoxic component of the (in the case of botulinum toxin type A) 900 kDa complex.

Any recombinant stabilizer which is present in a pharmaceutical composition within the scope of my invention can be a recombinant albumin, a recombinant collagen, a recombinant gelatin and/or other recombinant primary stabilizer. The pharmaceutical composition can also comprise a secondary stabilizer, such as a metal (i.e. zinc) or NAT.

Significantly, a pharmaceutical composition within the scope of my invention can have an enhanced potency or stability. By enhanced potency it is meant that the potency of a first botulinum toxin pharmaceutical composition is greater than the potency of a second botulinum toxin pharmaceutical composition. For example a first botulinum toxin pharmaceutical composition can have a particular ratio (such as 28:1) of two excipients (such as albumin and sodium chloride) present in the first composition. A second botulinum toxin pharmaceutical composition can have a known ratio (such as about 0.6:1) of the same two excipients (i.e. albumin and sodium chloride) present in the second composition. Potency and relative potencies can be determined by a method used to determine a biological activity of a botulinum toxin, such as a mouse $LD_{50}$ assay. Generally, greater potency means that a lesser amount (i.e. fewer units) of a botulinum toxin pharmaceutical composition is required to paralyze a muscle. Preferably, a first botulinum toxin pharmaceutical composition has at least a 5% greater potency (and as much as a 50% greater potency) than does the second botulinum toxin pharmaceutical composition.

A pharmaceutical composition within the scope of the present invention can also include a neurotoxin, and a polysaccharide. The polysaccharide stabilizes the neurotoxin. The pharmaceutical compositions disclosed herein can have a pH of between about 5 and 7.3 when reconstituted or upon injection.

The pharmaceutical composition is suitable for administration to a human patent to achieve a therapeutic effect, and the neurotoxin can be one of the botulinum toxin serotypes A, B, $C_1$, D, E, F and G.

A further embodiment of the present invention is a method for using a pharmaceutical composition, the method comprising the step of local administration of the pharmaceutical composition to a patient to achieve a therapeutic or cosmetic effect.

Particular Pharmaceutical Compositions

My invention encompasses a pharmaceutical composition comprising: (a) a botulinum toxin; (b) a first excipient, wherein the first excipient is an albumin, and;

(c) a second excipient, (d) wherein the weight to weight ratio of the first excipient to the second excipient present in the pharmaceutical composition is greater than 0.6 and less than about 100. The potency of the botulinum toxin in this pharmaceutical composition can be between about 5% greater and about 200% greater than the potency of a botulinum toxin in a comparison pharmaceutical composition. The comparison pharmaceutical composition can contain: (a) the same amount and type of botulinum toxin, and; (b) the same first and second excipients, as does the pharmaceutical composition, and; (c) the first and second excipients can be are present in the comparison pharmaceutical composition in a weight to weight ratio of 0.6 or less.

Additionally, the potency of the botulinum toxin in the pharmaceutical composition can be between about 10% greater and about 100% greater than the potency of the botulinum toxin in the comparison pharmaceutical composition, In this pharmaceutical composition the botulinum toxin is present as a botulinum toxin complex or the botulinum toxin can be present as a pure botulinum toxin (i.e. as a neurotoxic component with a molecular weight of about 150 kiloDaltons, and at substantially free of the botulinum toxin complex proteins).

The first excipient in the pharmaceutical composition can be a serum albumin or a recombinant albumin. The second excipient in the pharmaceutical composition can be sodium chloride. The weight to weight ratio of the first excipient to the second excipient present in the pharmaceutical composition is between about 1 and about 50.

A detailed embodiment of a pharmaceutical composition within the scope of my invention can comprise: (a) between about $2.0 \times 10^{-11}$ grams and about $3.5 \times 10^{-11}$ grams of a botulinum toxin type A for each unit of botulinum toxin present in the pharmaceutical composition, the unit of the botulinum toxin being determined by a mouse $LD_{50}$ potency assay; (b) an albumin, and (c) sodium chloride, (d) wherein the weight to weight ratio of the albumin to the sodium chloride present in the pharmaceutical composition is greater than 0.6 and less than about 100. The potency of the botulinum toxin in the pharmaceutical composition can be between about 5% greater and about 200% greater than the potency of a botulinum toxin in a comparison pharmaceutical composition, which comparison pharmaceutical composition contains (a) the same amount and type of botulinum toxin, and (b) the same albumin and sodium chloride, as does the pharmaceutical composition of claim 10, and (c) the albumin and sodium chloride are present in the comparison pharmaceutical composition in a weight to weight ratio of 0.6 or less. The potency of the botulinum toxin in the pharmaceutical composition can be between about 10% greater and about 100% greater than the potency of the botulinum toxin in the comparison pharmaceutical composition. Alternately, the weight to weight ratio of the albumin to the sodium, chloride present in the pharmaceutical composition can between about 1 and about 50.

My invention also encompasses a process for making a pharmaceutical composition by (a) combining about 2.5 ng of a botulinum toxin type A complex with an albumin and sodium chloride in a weight to weight ratio of the albumin to the sodium chloride in the pharmaceutical composition of greater than 0.6 and less than about 100, to form a mixture, and; (b) vacuum drying the mixture, to thereby obtain a pharmaceutical composition with a potency after reconstitution of between about 70 units and about 130 units. This process can further comprise the step, before the vacuum drying step, of lyophilizing the mixture. A useful pharmaceutical composition can be made by this process.

My invention also encompasses a pharmaceutical composition suitable for administration to a human, comprising: (a) a botulinum toxin; (b) sodium chloride, and; (b) a stabilizer, wherein the potency of the botulinum toxin present in the pharmaceutical composition is about 40 units/ng. The weight to weight ratio of the albumin to the sodium chloride present in this pharmaceutical composition can be greater than 0.6 and less than about 100. The stabilizer can be a recombinant stabilizer, such as a recombinant albumin, a recombinant collagen and/or a recombinant gelatin. The botulinum toxin can be selected from the group consisting of botulinum toxins types A, B, C, D, E, and F.

My invention also encompasses a pharmaceutical composition suitable for administration to a human, comprising: (a) a botulinum toxin; (b) sodium chloride, and; (b) an albumin, wherein the potency of the botulinum toxin present in the pharmaceutical composition is between about 24 units/ng and about 60 units/ng. The weight to weight ratio of the albumin to the sodium chloride can be greater than 0.6 and less than about 100.

My invention also encompasses a pharmaceutical composition suitable for administration to a human, comprising: (a) a botulinum toxin; (b) sodium chloride, and;
(b) an albumin, wherein the weight to weight ratio of the albumin to the sodium chloride present in the pharmaceutical composition is between about 1 and about 40 and the potency of the botulinum toxin present in the pharmaceutical composition is between about 24 units/ng and about 60 units/ng.

My invention also encompasses a process for making a botulinum toxin pharmaceutical composition which has a potency of between about 30 to 40 units/ng and is suitable for administration to a human, the process comprising the steps of: (a) adding a botulinum toxin type A complex which has a potency of between about 30-40 units/ng to albumin and sodium chloride in a weight to weight ratio of about 1 to about 40, to form a mixture; (b) vacuum drying or lyophilizing the mixture, and; (c) reconstituting the mixture with normal saline, to thereby obtain a botulinum toxin pharmaceutical composition which has a potency of between about 30-40 units/ng.

Finally, my invention also encompasses a method for treating a therapeutic or cosmetic condition, the method comprising the step of administering to a mammal a botulinum toxin pharmaceutical composition which has a potency of about 40 units/ng.

The foregoing methods may be practiced and the compositions made using a composition that comprises a botulinum toxin type A. In other embodiments of the invention, the foregoing methods may be practiced with a composition that comprises botulinum toxin type B. In further embodiments of the invention, the methods may be practiced with a composition that comprises a plurality of botulinum toxin serotypes, such as botulinum toxin serotypes selected from the group consisting of botulinum toxin serotypes A, B, $C_1$, D, E, F and G. In certain embodiments of the invention, purified botulinum toxins may be used. In other embodiments, modified botulinum toxins may be used. The compositions used in the foregoing methods may also include one or more amino acids in addition to the botulinum toxin and the polysaccharide. Embodiments of the invention disclosed herein can be administered intramuscularly (into or to the vicinity of a striated, smooth or cardiac muscle), intradermally, topically, subcutaneously, into or to the vicinity of a gland, into a lumen of the body (such as into a bladder lumen) and/or intrathecally.

DRAWINGS

The following drawings illustrate aspects of my invention.

FIG. 1 is a diagramatic representation of a 900 kiloDalton botulinum toxin complex.

FIG. 2 is a graph which shows the mouse $LD_{50}$ potency after reconstitution (on the Y-axis) of lyophilized, vacuum-dried botulinum toxin formulations made with 2.5 ng of botulinum toxin, 500μ of HSA and from zero to 10N (9000 μg) of NaCl.

Figure 3:
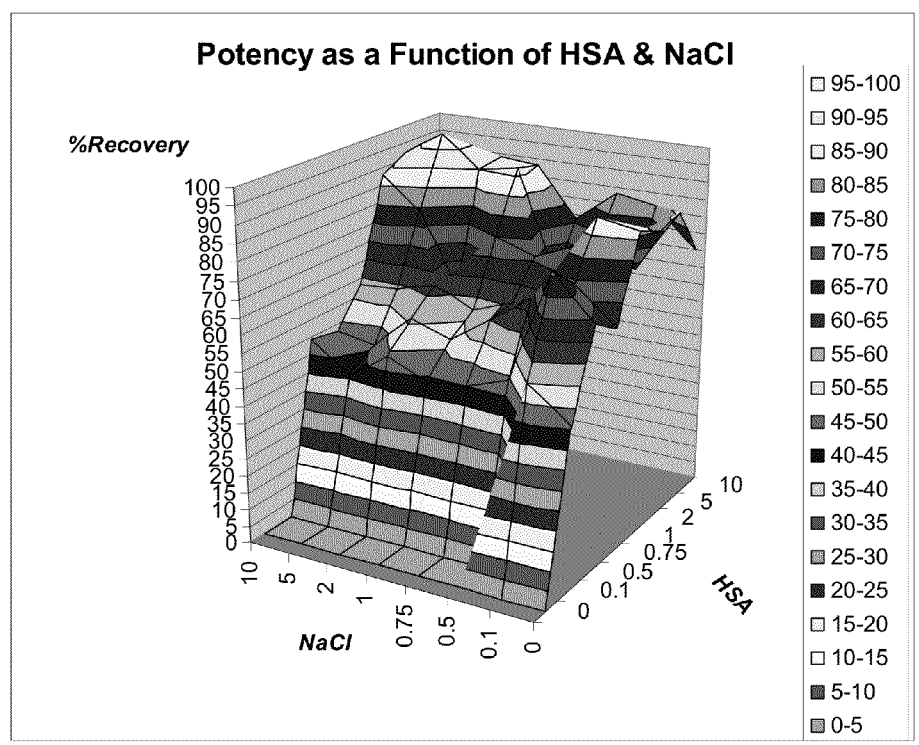

FIG. 3 presents in three axes recovered potency data for a number of experimental botulinum toxin formulations. The X axis of FIG. 3 represents the amount of sodium chloride (NaCl) present in experimental or research vial preparations in multiples of the sodium chloride normalized (N) against the 900 μg NaCl content in a 100 unit vial of Botox®. Thus, the integer one on the X axis in FIG. 1 represents 900 μg of NaCl. The Y axis of FIG. 3 represents the amount of human serum albumin (HSA) present in the same experimental vial preparations in multiples of the HSA normalized against the 500 μg HSA content in a 100 unit Vial of Botox®. Thus, the integer one on the Y axis in FIG. 3 represents 500 μg of HSA. The Z axis of FIG. 3 represents the recovered potency of these vacuum-dried experimental botulinum toxin compositions, where each vial contained exactly the same amount of botulinum toxin (2.5 ng) and where each botulinum toxin pharmaceutical composition was reconstituted with the same amount of normal saline, and it's potency after reconstitution determined by the mouse $LD_{50}$ assay.

DESCRIPTION

The present invention is based upon the discovery that a stable botulinum toxin with an enhanced potency can be made with a particular ratio of excipients in a botulinum toxin pharmaceutical composition.

I have discovered that the potency of a botulinum toxin in a botulinum toxin pharmaceutical composition can be increased significantly by formulating the botulinum toxin pharmaceutical composition with particular ratios of the excipients in the botulinum toxin pharmaceutical composition. Such particular excipient ratios permit obtaining a botulinum toxin pharmaceutical composition which has a higher potency than does a botulinum toxin pharmaceutical composition with different excipient ratios. For example, my invention permits a botulinum toxin pharmaceutical composition to be prepared with a higher potency per nanogram botulinum toxin present in the botulinum toxin pharmaceutical composition, than the potency of a botulinum toxin pharmaceutical composition with different excipient ratios.

The botulinum toxin present in the botulinum toxin pharmaceutical composition can be a native, recombinant, hybrid, chimeric or modified botulinum toxin type A, B, C, D, E, F or G. Additionally, the botulinum toxin can be present in the botulinum toxin pharmaceutical composition as either a complex or as a pure botulinum toxin. A botulinum toxin complex comprises a botulinum toxin molecule (about 150 kDa) and one or more non-toxic haemagluttinin and/or non-toxic non-haemagluttinin proteins. The complex can have a molecular weight of, for example, 300, 600 or 900 kDa, with the amount in excess of 150 kDa being attributed to the non-toxic haemagluttinin and/or non-toxic non-haemagluttinin protein components of the complex. The 150 kDa botulinum toxin molecule is also referred to as the neurotoxic component and as pure botulinum toxin.

An excipient that can be present in a botulinum toxin pharmaceutical composition can be a protein such as an albumin, such as a human serum albumin or a recombinantly made albumin. Another excipient that can be present in a botulinum toxin pharmaceutical composition can be sodium chloride. Albumin and sodium chloride can be used as stabilizing excipients in a botulinum toxin pharmaceutical composition. It is known to use of sodium chloride and albumin as bulking agents in a botulinum toxin pharmaceutical composition. The albumin is used as an excipient to stabilize the toxin during drying and to prevent the toxin from adhering to surfaces, such as the glass surfaces onto which the toxin can come into contact during manufacture and storage. See e.g., Rader R. A., *Botulinum toxin A*, in Ronald Rader, ed. *BIOPHARMA: Biopharmaceutical Products in the U.S. Market* Rockville, Md.: Biotechnology Information Institute; 2001: pp. 271-274 (332), and; Rader R. A., *Botulinum toxin B*, in Ronald Rader, ed. *BIOPHARMA: Biopharmaceutical Products in the U.S. Market* Rockville, Md.: Biotechnology Information Institute; 2001:pp. 274-276 (333).

An embodiment of my invention is a botulinum toxin pharmaceutical composition with particular ratios of the albumin to the sodium chloride present in a botulinum toxin pharmaceutical compositions. I have found that such ratios permit a significantly increase in the potency of a reconstituted lyophilized or vacuum dried botulinum toxin pharmaceutical composition.

There are a number of reasons why it would not be expected that altering a ratio of excipients present in a botulinum toxin pharmaceutical composition would increase the potency of the botulinum toxin, and why one would expect just the opposite to occur.

First, botulinum toxin is a relatively large protein for incorporation into a pharmaceutical formulation (the molecular weight of the botulinum toxin type A complex is 900 kD) and is therefore is inherently fragile and labile. The size of the toxin complex makes it much more friable and labile than smaller, less complex proteins, thereby compounding the formulation and handling difficulties if toxin stability is to be maintained. Hence, altering a ratio of excipients present in a botulinum toxin pharmaceutical composition would be expected to denature, fragment or otherwise detoxify the toxin molecule or cause disassociation of the non-toxin proteins present in the toxin complex.

Second, as the most lethal known biological product, exceptional safety, precision, and accuracy is called for at all steps of the formulation of a botulinum toxin containing pharmaceutical composition. Thus, altering a ratio of excipients present in a botulinum toxin pharmaceutical composition would be expected to exacerbate or to interfere with the already extremely stringent botulinum toxin containing pharmaceutical composition formulation requirements.

Third, since botulinum toxin was the first microbial toxin to be approved (by the FDA in 1989) for injection for the treatment of human disease, specific protocols had to be developed and approved for the culturing, bulk production, formulation into a pharmaceutical and use of botulinum toxin. Important considerations are toxin purity and dose for injection. Hence, altering a ratio of excipient present in a botulinum toxin pharmaceutical composition would be expected to interfere with toxin purity and dosage requirements.

Fourth, particular difficulties exist to stabilize botulinum toxin type A, because type A consists of a toxin molecule of about 150 kD in noncovalent association with nontoxin proteins weighing about 750 kD. The nontoxin proteins are believed to preserve or help stabilize the secondary and tertiary structures upon which toxicity is dependant. Procedures or protocols applicable to the stabilization of nonproteins or to relatively smaller proteins are not applicable to the problems inherent with stabilization of the botulinum toxin complexes, such as the 900 kD botulinum toxin type A complex. Thus while from pH 3.5 to 6.8 the type A toxin and non toxin proteins are bound together noncovalently, under slightly alkaline conditions (pH>7.1) the very labile toxin is released from the toxin complex. As set forth previously, pure botulinum toxin (i.e. the 150 kD molecule) has been proposed as the active ingredient in a pharmaceutical composition. Thus, altering a ratio of excipient present in a botulinum toxin pharmaceutical composition would be expected to upset this fragile toxin stability equilibrium.

I found that within certain ranges when albumin concentrations were increased as compared to the sodium chloride concentration, the potency of the reconstituted botulinum toxin pharmaceutical composition increased. I also found that within certain ranges when sodium chloride concentrations were increased as compared to the albumin concentration, the potency of the reconstituted botulinum toxin pharmaceutical composition decreased. Surprisingly, a high (absolute) concentrations of sodium chloride were found to not be deleterious to potency after reconstitution as long as a certain ratio of the sodium chloride to the albumin was maintained. Thus, I discovered that there exist optimal sodium chloride to albumin ratios (irrespective of the absolute amounts of sodium chloride or of albumin present) at which an increased potency of the botulinum toxin pharmaceutical composition after reconstitution can be obtained.

As set forth above, I have discovered that establishing particular sodium chloride to albumin ratios in a botulinum toxin pharmaceutical composition prior to lyophilization or freeze drying can be used to optimize the potency of the reconstituted botulinum toxin pharmaceutical composition.

Significantly, I also discovered that reconstitution of the botulinum toxin pharmaceutical composition with normal saline (0.9%), the typical reconstitution fluid, does not affect the optimization of the potency botulinum toxin pharmaceutical composition obtaining by established certain sodium chloride to albumin ratios in the botulinum toxin pharmaceutical composition prior to its lyophilization or freeze drying. This discovery therefore permits conservation of the tonicity of the reconstituted botulinum toxin pharmaceutical composition administered to a patient, Without wishing to be bound by theory, it can be hypothesized that establishment of certain sodium chloride to albumin ratios in the botulinum toxin pharmaceutical composition prior to its lyophilization or freeze drying permits obtaining an optimized potency of the botulinum toxin pharmaceutical composition after it's reconstitution by providing a hospitable chemical and physical environment for the botulinum toxin during the processing (compounding or formulation) steps or procedures while also reducing adsorption of the botulinum toxin upon contact surfaces (such as glass vials). Presumably, processing of a botulinum toxin pharmaceutical composition with non-optimized ratios of sodium chloride and albumin damages the botulinum toxin molecule and increases it's adsorption to surfaces.

Thus, changing the NaCl/HSA ratio to a particular ratio may increase toxin potency because less toxin is thereafter lost during freezing to denaturation and adsorption to surfaces (these two phenomenon may be related, e.g., denaturation caused by adsorption). HSA can act as a cryoprotectant and NaCl as a degradant. Typically, some amount of a botulinum toxin will adhere to glass surface. I have determined that when less NaCl is present in a botulinum toxin pharmaceutical composition, the vacuum-dried toxin does not adhere to a glass surface, thereby indicating that NaCl can facilitate or cause adsorption of the toxin to processing or storage surfaces. Thus particular HSA:NaCl ratios can be optimal because they permit the HSA to provide sufficient cryoprotection while at the same time counteracting a deleterious effect (surface adsorption) caused by of the NaCl present.

Thus, my discovery permits a botulinum toxin pharmaceutical composition to be made with a potency that is essentially 100% of the theoretically possible potency. Additionally the optimized potency is maintained after reconstitution with saline, which permits administration of an isotonic botulinum toxin pharmaceutical composition. The result is a more efficient manufacturing use of the botulinum toxin active ingredient and a reduced patient exposure to degraded botulinum toxin in the final botulinum toxin pharmaceutical composition.

A significant advantage of my invention is that it permits a botulinum toxin pharmaceutical composition to be manufactured (compounded from a raw or bulk botulinum toxin) with considerably less botulinum toxin. This permits a more efficient manufacturing process in which less bulk toxin is used to make the final botulinum toxin pharmaceutical composition. Additionally, because the final botulinum toxin pharmaceutical composition contains less botulinum toxin, the patient, on a unit to unit basis, is administered less botulinum toxin with the ensuing advantages of fewer side effects, such as reduced immunogenicity. Specifically, my invention permits a botulinum toxin pharmaceutical composition to be made with the same potency but with from about 5% less to about 50% less total botulinum toxin present in the botulinum toxin pharmaceutical composition. For example, a botulinum toxin pharmaceutical composition which formerly comprised about 20 units of botulinum toxin for each 1 ng of botulinum toxin present can, according to my invention, now be made with as much as 40 units of botulinum toxin for each 1 ng of botulinum toxin present in the botulinum toxin pharmaceutical composition.

A botulinum toxin pharmaceutical composition manufacturing (compounding) process can typically require as much as a 50% overage, meaning that the manufacturing process which is initiated with a 1.5× amount (i.e. 150 units) of a botulinum toxin provides a botulinum toxin pharmaceutical composition with an amount 1× (i.e. 100 units) of the botulinum toxin. A manufacturing or compounding process is the process by which a botulinum toxin (referred to as bulk or raw toxin) obtained from bacterial fermentation is then diluted, compounded and processed for the preparation of a botulinum toxin pharmaceutical composition suitable for administration to humans for therapeutic and/or cosmetic purposes.

Thus, there is an unexplained loss of up to 50% of the potency of the botulinum toxin during the compounding process. It has been postulated that the 50% overage is required due to denaturation and/or loss of botulinum toxin during the compounding process. My invention indicates that the up to 50% overage of botulinum toxin is not lost during compounding, but rather the chemical composition of the formulation is the critical parameter in achieving full recovery of toxin in the finished product. No overage is necessary when optimized ratios of the excipients are used by providing the appropriate environment during the vacuum-drying process. While not wanting to be bound by theory, it is plausible that optimal ratios reduce adsorption to surfaces and denaturation during the drying process.

Thus, my invention permits a botulinum toxin pharmaceutical composition to be made with eg from about 34% less (if the amount of botulinum toxin in a 100 unit vial is reduced from 3.8 ng to 2.5 ng) to about 48% less (if the amount of toxin in a 100 unit vial is reduced from 4.8 ng to 2.5 ng, to about to about 50% less (if the amount of toxin in a 100 unit vial is reduced from 5.0 ng to 2.5 ng.

Human serum albumin (plasma derived) is available commercially from various sources, including, for example, from Bayer Corporation, pharmaceutical division, Elkhart, Ill., under the trade name Plasbumin®. Plasbumin® is known to contain albumin obtained from pooled human venous plasma as well as sodium caprylate (a fatty acid, also known as octanoate) and acetyltryptophan ("NAT"). See e.g. the Bayer Plasbumin®-20 product insert (directions for use) supplied with the product and as published at web site actsysmedical.com/PDF/plasbumin20.pdf. The caprylate and acetyltryptophan in commercially available human serum albumin are apparently added by FDA requirement to stabilize the albumin during pasteurization at 60 degrees C. for 10 hours prior to commercial sale. See e.g. Peters, T., Jr., *All About Albumin Biochemistry, Genetics and Medical Applications*, Academic Press (1996), pages 295 and 298. Recombinant human albumin is available from various sources, including for example, from Bipha Corporation of Chitose, Hokkaido, Japan, Welfide Corporation of Osaka, Japan, and from Delta Biotechnology, Nottingham, U.K., as a yeast fermentation product, under the trade name Recombumin®.

It is known to express recombinant human serum albumin (rHSA) in the yeast species *Pichia pastoris*. See e.g. Kobayashi K., et al., *The development of recombinant human serum albumin*, Ther Apher 1998 November; 2(4):257-62, and; Ohtani W., et al., *Physicochemical and immunochemical properties of recombinant human serum albumin from Pichia pastoris*, Anal Biochem 1998 Feb. 1; 256(1):56-62. See also U.S. Pat. No. 6,034,221 and European patents 330 451 and 361 991. A clear advantage of a rHSA is that it is free of blood derived pathogens.

The excipient ratios set forth herein can it is believed help to provide stability to a neurotoxin active ingredient, such as a botulinum toxin, present in the pharmaceutical composition by: (1) reducing adhesion (commonly referred to as "stickiness") of the botulinum toxin to surfaces, such as the surfaces of laboratory glassware, vessels, the vial in which the pharmaceutical composition is reconstituted and the inside surface of the syringe used to inject the pharmaceutical composition. Adhesion of the botulinum toxin to surfaces can lead to loss of botulinum toxin and to denaturation of retained botulinum toxin, both of which reduce the toxicity of the botulinum toxin present in the pharmaceutical composition; (2) reducing the denaturation of the botulinum toxin and/or dissociation of the botulinum toxin from other non-toxin proteins present in the botulinum toxin complex, which denaturation and/or dissociation activities can occur because of the low dilution of the botulinum toxin present in the pharmaceutical composition (i.e. prior to lyophilization or vacuum drying) and in the reconstituted pharmaceutical composition; (3) reducing loss of botulinum toxin (i.e. due to denaturation or dissociation from non-toxin proteins in the complex) during the considerable pH and concentration changes which take place during preparation, processing and reconstitution of the pharmaceutical composition.

The three types of botulinum toxin stabilizations presumably provided by the ratios set forth herein can conserve and preserve the botulinum toxin with it native toxicity prior to injection of the pharmaceutical composition.

In certain embodiments of the invention, the pharmaceutical compositions of the invention may comprise a plurality of botulinum toxin serotypes. In other words, the composition may include two or more different botulinum toxin serotypes. For example, a composition may include botulinum toxin serotypes A and B. In another embodiment, a composition may include botulinum toxin serotypes A and E. Using a combination of botulinum toxin serotypes will permit caregivers to customize the composition to achieve a desired effect based on the condition being treated. In an additional embodiment of the invention, the composition may comprise a modified botulinum toxin. The modified botulinum toxin will preferably inhibit the release of neurotransmitter from a neuron, but may have a greater or lower potency than the native botulinum toxin, or may have a greater or lower biological effect than the native botulinum toxin. Because the compositions of the invention may be used for relatively long-term treatment of animals, the compositions may be provided in a relatively pure form. In one embodiment, the compositions are of a pharmaceutical grade. In certain embodiments, the clostridial neurotoxin has a greater than 95% purity. In additional embodiments, the clostridial neurotoxin has a purity greater than 99%.

My invention also encompasses addition of a preservative, either in the diluent or formulation itself, to allow extended storage. A preferred preservative is preserved saline containing benzyl alcohol.

A liquid formulation can be advantageous. A single-step presentation (e.g., pre-filled syringe) or a product configuration that the user perceives as a single-step presentation (e.g., dual-chambered syringe) would provide convenience by eliminating the reconstitution step. Freeze-drying is a complicated, expensive and difficult process. Liquid formulations are often easier and cheaper to produce. On the other hand liquid formulations are dynamic systems and therefore more susceptible to excipient interaction, fast reactions, bacterial growth, and oxidation than freeze-dried formulations. A compatible preservative might be needed. Anti-oxidants such as methionine might also be useful as scavengers especially if surfactants are used to reduce adsorption as many of these compounds contain or produce peroxides. Any of the stabilizing excipients which can be used in a freeze-dried formulation (e.g., hydroxyethyl starch or an amino acid such, lysine) might be adapted to use in a liquid formulation to assist in reducing adsorption and stabilize the toxin. Suspensions similar to those developed for insulin are also good candidates. Additionally, stabilizing botulinum toxin in a liquid vehicle might require a low pH vehicle as the toxin is reported to be labile above pH 7. This acidity could produce burning and stinging upon injection. A binary syringe could be employed. Inclusion of a co-dispensed buffer, sufficient to raise the pH to physiologic levels, would alleviate injection discomfort of a low pH while maintaining the toxin at a low pH during storage. Another dual-chambered syringe option would include diluent and lyophilized material segregated in separate chamber, only mixing upon use. This option provides the advantages of a liquid formulation without the additional resources and time.

As discussed herein, the neurotoxin may be prepared and purified using techniques well-known in the art. The purified toxin may subsequently be diluted in a stabilizer such as a polysaccharide (e.g., hetastarch), or a recombinant serum albumin, or a serum albumin of the species of animal receiving the neurotoxin. It is preferred that the stabilizer prevents or reduces denaturation of the toxin, and produces no, or minimal, immunogenic responses in the animal that will receive the toxin. Aliquots of the diluted toxin are then lyophilized using conventional procedures.

The lyophilized neurotoxin may be reconstituted before administering the neurotoxin to a subject by adding water, saline, or any buffer solution to the lyophilized neurotoxin. In certain embodiments, sodium free buffers may be preferred to help reduce denaturation of the neurotoxin.

The pharmaceutical compositions of the invention can be administered using conventional modes of administration. In preferred embodiments of the invention, the compositions are administered intramuscularly or subcutaneously to the subject. In other embodiments, the compositions of the invention may be administered intrathecally. In addition, the compositions of the invention may be administered with one or more analgesic or anesthetic agents.

The most effective mode of administration and dosage regimen for the compositions of this invention depends upon the type, severity, and course of the condition being treated, the animal's health and response to treatment, and the judgment of the treating doctor. Accordingly, the methods and dosages of the compositions should be tailored to the individual subject.

The compositions of the invention may also be injected into smooth muscles (as compared to striated muscles) to treat colonic, bladder, esophageal, or gastrointestinal dysfunction, including, but not limited to achalasia, anal fissure, hyperactive sphincter of oddi. The administration of the compositions may reduce or prevent unfavorable systemic consequences from treatment with drugs that do not specifically act on the organ of interest.

Compositions containing botulinum toxin may be administered intramuscularly, intrathecally, or subcutaneously to relieve pain experienced by the animal. These treatments are also restricted to the site of injection and have minimal side effects compared to current systemic approaches of treating these pain syndromes with pain relieving drugs.

Relief from pain by practicing the methods of the invention may be determined by observing the reduction in the number of symptoms that the animal is exhibiting. One or more of the symptoms may be reduced.

As indicated above, dosages of the neurotoxin, such as botulinum toxin, in the compositions may vary. In one embodiment, the compositions contain a therapeutically effective amount of neurotoxin, for example, between about 1 U and about 500 U of botulinum toxin type A. Preferably the amounts are between about 10 U and about 300 U. More preferably the amount is between about 20 U and 250 U, such about 50 U to 200 U, or 70 U.

Alternatively, botulinum toxin, such as botulinum toxin type A, can be administered in amounts between about $10^{-3}$ U/kg and about 60 U/kg to alleviate pain experienced by a mammal. Preferably, the botulinum toxin used is administered in an amount of between about $10^{-2}$ U/kg and about 50 U/kg. More preferably, the botulinum toxin is administered in an amount of between about $10^{-1}$ U/kg and about 40 U/kg. Most preferably, the botulinum toxin is administered in an amount of between about 1 U/kg and about 30 U/kg. In a particularly preferred embodiment of the present disclosed methods, the botulinum toxin is administered in an amount of between about 1 U/kg and about 20 U/kg.

Compositions containing other serotypes of botulinum toxin may contain different dosages of the botulinum toxin. For example, botulinum toxin type B may be provided in a composition at a greater dose than a composition containing botulinum toxin type A. In one embodiment of the invention, botulinum toxin type B may be administered in an amount between about 1 U/kg and 150 U/kg. Botulinum toxin type B may also be administered in amounts of up to 20,000 U (mouse units, as described above). In another embodiment of the invention, botulinum toxin types E or F may be administered at concentrations between about 0.1 U/kg and 150 U/kg. In addition, in compositions containing more than one type of botulinum toxin, each type of botulinum toxin can be provided in a relatively smaller dose than the dose typically used for a single botulinum toxin serotype. The combination of botulinum toxin serotypes may then provide a suitable degree and duration of paralysis without an increase in diffusion of the neurotoxins (e.g. see U.S. Pat. No. 6,087,327).

The compounding process used in the preparation of Botox® (a vacuum dried powdered pharmaceutical composition) begins with the entry of about 150 units of the bulk botulinum toxin into the compounding process. The final product (ready for reconstitution) comprises only about 100 units of the botulinum toxin (as well as specific amount of albumin and sodium chloride as excipients added during the compounding process). Thus, about 50 units of botulinum toxin (about one third of the amount of the botulinum toxin which entered into the compounding process) is lost during compounding, for example by denaturation, absorption and inactivation of the botulinum toxin onto processing surfaces. Hence, it has been necessary to start the compounding process with about a 50% overage (i.e. start with about 150 units of botulinum toxin in order to obtain product with about 100 units of botulinum toxin).

One hundred units of botulinum toxin typically comprises from about 3.6 ng to about 5 ng of botulinum toxin. I have discovered that by altering the ratio of the albumin and sodium chloride excipients used in the compounding process it is possible to: (1) remove the 50% overage factor, and; (2) on a nanogram to nanogram basis, obtain a more potent botulinum toxin. By eliminating the 50% overage factor in the compounding process, one can have about 100 units of botulinum toxin enter the compounding process and yet at the completion of the compounding process still obtain product with about 100 units of botulinum toxin. Additionally, one can obtain a 100 botulinum toxin unit product comprising only about 2.4 ng of botulinum toxin, as compared to the previously required 3.6 to 5 ng of botulinum toxin required to obtain a 100 unit botulinum toxin product. Thus, the potency of the botulinum toxin which was previously as low as about 20 units per ng (100 units divided by 5 ng) can now be increased to as high as about 42 units per ng (100 units divided by 2.4 ng), which equates to an increase of potency of about 110%.

Commercially available botulinum toxin pharmaceutical compositions approved by regulatory agencies for use in humans to treat one or more indications include BOTOX® (Allergan, Inc, Irvine, Calif.), Dysport® (Ipsen Pharmaceuticals, Paris, France) and MyoBloc™ (Solstice Neurosciences, San Diego, Calif.).

EXAMPLES

The following non-limiting examples provide those of ordinary skill in the art with specific preferred formulations and methods and are not intended to limit the scope of the invention.

In the Examples below the well known mouse lethal dose$_{50}$ assay (the "MLD50") was used to determine recovered potency of the botulinum toxin formulations made. The MLD50 is a method for measuring the potency of a botulinum toxin by intraperitoneal injection of the botulinum toxin into female mice (about four weeks old) weighing 17-22 grams each at the start of the assay. Each mouse is held in a supine position with its head tilted down and is injected intraperitoneally into the lower right abdomen at an angle of about 30 degrees using a 25 to 27 gauge ⅜" to ⅝" needle with one of several serial dilutions of the botulinum toxin in saline. The death rates over the ensuing 72 hours for each dilution are recorded. The dilutions are prepared so that the most concentrated dilution produces a death rate of at least 80% of the mice injected, and the least concentration dilution produces a death rate no greater than 20% of the mice injected. There must be a minimum of four dilutions that fall within the monotone decreasing range of the death rates. The monotone decreasing range commences with a death rate of no less than 80%. Within the four or more monotone decreasing rates, the two largest and the two smallest rates must be decreasing (i.e. not equivalent). The dilution at which 50% of the mice die within the three day post injection observation period is defined as a dilution which comprises one unit (1 U) of the botulinum toxin.

In the Tables which follow "normalized" means with regard to the amount used in a 100 unit vial of Botox®.

Example 1

High Potency Botulinum Toxin Formulations (Research Method) With Various Ratios of Sodium Chloride to Albumin An experiment was carried out to assess the recovered potency of numerous botulinum toxin research vial formulations with the same amount of botulinum toxin type A complex in each formulation, but with different amounts of HSA and NaCl present in the each formulation. Thus, while 2.5 ng of the botulinum toxin was used consistently per vial, each formulation vial contained from 0N (0 μg) of HSA to 10N (5000 μg) of HSA, and from 0N (0 μg) of NaCl to 10N (9000 μg) of NaCl.

The data in Table 1 was obtained using research lot preparation procedures. Thus, the Table 1 data was obtained by mixing one of the specified seven different amounts of sodium chloride (NaCl) (from a 0.1N amount of 90 μg per vial to a 10N amount of 9000 μg per vial) with one of the specified three different amounts of human serum albumin (HSA) (Bayer) (from a 0.5N amount of 250 μg per vial to a 1N amount of 500 μg per vial) with sterile water and the same amount (2.5 ng/vial) of botulinum toxin type A complex so as to prepare experimental or research botulinum toxin pharmaceutical composition vials. These vials were then placed in a lyophilizer, vacuum-dried and stoppered. The vials were then reconstituted with normal saline and tested for recovered potency using a refined version of the mouse potency LD50 assay.

Significantly, Table 1 shows that, as compared to the Botox® equivalent research formulation (that is, the research vial formulation which contained 500 μg of HSA, 900 μg of NaCl and 2.5 ng of botulinum toxin type A complex, and had a recovered potency of 57 units)), a high potency (61 to 89 units of botulinum toxin activity per vial, that is from 107% to 156% greater than the potency of the Botox® equivalent research formulation) was obtained for each of the six formulations which had HSA:NaCl ratios greater than 0.6 (the HSA: NaCl ratios in Table 1 that were greater than 0.6 were ratios from 0.7 to 5.6.

The Table 1 data therefore shows that a high potency botulinum toxin formulation can be obtained by increasing the HSA:NaCl ratio of the formulation.

TABLE 1

Potency of Botulinum Toxin Formulations with HSA:NaCl Ratios from 0.03 to 5.6

| Normalized NaCl (μg/vial) | Normalized HSA (μg/vial) | | |
|---|---|---|---|
| | 0.5 (250) | 0.75 (375) | 1 (500) |
| 0.1 (90) | 81 (2.8) | 74 (4.2) | 89 (5.6) |
| 0.5 (450) | 49 (0.6) | 68 (0.8) | 64 (1.1) |
| 0.75 (675) | 45 (0.4) | 60 (0.6) | 61 (0.7) |
| 1 (900) | 44 (0.3) | 52 (0.4) | 57 (0.6) |
| 2 (1800) | 49 (0.1) | 56 (0.2) | 62 (0.3) |
| 5 (4500) | 41 (0.06) | 46 (0.08) | 59 (0.1) |
| 10 (9000) | 49 (0.03) | 48 (0.04) | 58 (0.06) |

A further example showing the potency of reconstituted research formulations made according to the procedures set forth in this Example 1 is provided by Table 2 below and by FIG. 2. Table 2 shows that formulations which contained a constant 1N (500 μg) amount of HSA, 2.5 ng of botulinum toxin and amounts of NaCl which varied from zero to 10N (9000 μg) had a potency which did not vary significantly as the HSA:NaCl ratio was decreased below 0.6, but that the potency of the formulation increased from about 57 units to about 90 units, as the HSA:NaCl ratio was increased from 0.6 to about 5.6.

TABLE 2

Potency of Botulinum Toxin Formulations with 1N and HSA:NaCl Ratios from 0.06 to 5.6

| Normalized Amount of NaCl | HSA:NaCl ratio | Potency |
|---|---|---|
| 10 | 0.06 | 59 |
| 5 | 0.1 | 60 |
| 2 | 0.3 | 61 |
| 1 | 0.6 | 58 |
| 0.75 | 0.7 | 62 |
| 0.5 | 1.1 | 65 |
| 0.1 | 5.6 | 89 |

FIG. 2 is a graphical representation of the Table 2 data.

FIG. 3 presents a combined view in three axes of the data generated by this Example 1. FIG. 3 shows that as the HSA:NaCl ratio is increased beyond about 0.6 (by either: (a) holding the amount of HSA in the formulation constant [at an amount between 0 and 10N] and decreasing the amount of NaCl in the formulation [from 10N to 0], or by; (b) holding the amount of NaCl constant and increasing the amount of HSA in the formulation), generally the recovered potency of the formulation increases. The amount of botulinum toxin in all the formulations used to generate the FIG. 3 data was constant at 2.5 ng per vial.

Example 2

High Potency Botulinum Toxin Formulations (Commercial Method) With Particular Ratio of Sodium Chloride to Albumin A further experiment was carried out in which botulinum toxin pharmaceutical compositions were made (compounded) using botulinum toxin type A complex, sodium chloride and human serum albumin. Botulinum toxin pharmaceutical compositions containing differing ratios of sodium chloride to the HSA were compounded using commercial manufacturing lot procedures. The compositions were then either lyophilized and vacuum dried to a solid, powder) state, followed by reconstitution with saline and mouse $LD_{50}$ recovered potency evaluation.

Results obtained are set forth in Table 3. The Table 3 data was obtained as follows: for the BOTOX data (last row in Table 3) 100 units vials of Botox® were reconstituted with normal saline followed by use of the mouse $LD_{50}$ assay to measure potency. The 1N HSA, 2N HSA, 5N HSA and 10N HSA represent formulations compounded in the same way used for the manufacture of Botox® and with the same excipients, reconstituted in the same manner, and potency assessed using the same mouse $LD_{50}$ assay, with only the following changes:

(1) one (1N), two (2N), five (5N) or ten times (10N) as much HSA was used in the compounding process for the manufacture of these four botulinum toxin type A complex formulations, as compared to how much HSA is used in the manufacture of Botox®. Thus, as shown in Table 3, the 1N (1N meaning normalized to contain the same amount of that excipient as is present in a 100 unit vial of Botox®) formulation was compounded to contain 500 μg of HSA, while the 10N formulation was compounded to contain 5000 μg of HSA.

(2) the amount of botulinum toxin type A complex used in each of the four 1N HSA, 2N HSA, 5N HSA and 10N HSA formulations was 2.4 ng.

(3) the amount of sodium chloride used in the compounding process for the manufacture of each of the four botulinum toxin type A complex formulations was altered so as to provide, a constant weight to weight ratio the HSA to the NaCl in the formulation of 28. Thus, in each of these four formulations the HSA:NaCl ratio was 47 times what it is for Botox® (28 vs 0.6).

Significantly, Table 3 shows that a high potency (95 to 103 units of botulinum toxin activity per vial) was obtained for each of the four HSA:NaCl ratio of 28 botulinum toxin formulations, and that this high potency was obtained upon use of from about 33% to about 52% less botulinum toxin (as compared to use of from about 3.6 ng to about 5 ng of botulinum toxin per vial of Botox®).

Additionally, as shown by Table 3, through wide ranges of the absolute amounts of HSA and sodium chloride present, a weight to weight ratio of HSA to sodium chloride of 28 consistently permitted a potency of about 40 units per ng of the compounded and reconstituted botulinum toxin to be obtained.

TABLE 3

Potency of Botulinum Toxin Formulations with an HSA:NaCl ratio of 28

|  | HSA:NaCl Wt. Ratio | Toxin (ng/vial) | NaCl (µg/vial) | HSA (µg/vial) | Potency (n = 2) |
|---|---|---|---|---|---|
| 1N HSA | 28 | 2.4 | 18 | 500 | 96 |
| 2N HSA | 28 | 2.4 | 36 | 1000 | 103 |
| 5N HSA | 28 | 2.4 | 90 | 2500 | 98 |
| 10N HSA | 28 | 2.4 | 180 | 5000 | 95 |
| BOTOX | 0.6 | 3.6 to 5 | 900 | 500 | 70-100 |

Thus, this experiment showed that the manufacturing (compounding) process 50% overage can be eliminated by altering the composition ratio of the formulation while still using existing manufacturing processes and excipients A pharmaceutical composition according to the invention disclosed herein has many advantages, including that the pharmaceutical composition can have high stability and high % recovery of toxin potency comparable to or superior to that achieved with currently available pharmaceutical compositions.

Various publications and/or references have been cited herein, the contents of which, in their entireties, are incorporated herein by reference.

Although the present invention has been described in detail with regard to certain preferred methods, other embodiments, versions, and modifications within the scope of the present invention are possible. For example, a wide variety of stabilizing polysaccharides, proteins and amino acids are within the scope of the present invention.

Accordingly, the spirit and scope of the following claims should not be limited to the descriptions of the preferred embodiments set forth above.

I claim:

1. A lyophilized pharmaceutical composition comprising: (a) a botulinum toxin type A; (b) an albumin, and (c) a polysorbate, (d) wherein the composition components are mixed and lyophilized, and the weight to weight ratio of the albumin to the polysorbate present in the pharmaceutical composition is greater than 0.6 and less than about 100, wherein the albumin is a recombinant albumin and wherein the botulinum toxin is present as a botulinum toxin complex.

2. A lyophilized pharmaceutical composition comprising: (a) a botulinum toxin type A; (b) an albumin, and (c) a polysorbate, (d) wherein the composition components are mixed and lyophilized, and the weight to weight ratio of the albumin to the polysorbate present in the pharmaceutical composition is greater than 0.6 and less than about 100 wherein the albumin is a recombinant albumin and wherein the botulinum toxin is present as a pure botulinum toxin.

3. A lyophilized pharmaceutical composition, comprising: (a) a botulinum toxin; (b) a first excipient, and; (c) a second excipient; wherein the first excipient is an albumin and the second excipient is a polysorbate, wherein the weight to weight ratio of the first excipient to the second excipient is greater than 0.6 and less than about 100, and further wherein the potency of the botulinum toxin in the lyophilized pharmaceutical composition is between about 5% greater and about 200% greater than the potency of a botulinum toxin in a comparison pharmaceutical composition comprising (a) the same amount and type of the botulinum toxin, (b) the same first excipient and second excipient, and (c) the first excipient and the second excipient are present in a weight to weight ratio of 0.6 or less.

4. The pharmaceutical composition of claim 3, wherein the albumin is a serum albumin.

5. The pharmaceutical composition of claim 3, wherein the albumin is a recombinant albumin.

6. The lyophilized pharmaceutical composition of claim 3, wherein the potency of the botulinum toxin in the pharmaceutical composition is between about 10% greater and about 100% greater than the potency of the botulinum in the comparison pharmaceutical composition.

* * * * *